United States Patent [19]

Garzia

[11] 3,969,520
[45] July 13, 1976

[54] 2-AMINO-4[2-(1-LOWER ALKYL-5-NITRO-2-IMIDIAZOLYL)VINYL]PYRIMIDINES FOR TREATING PROTOZOAL AND BACTERIAL INFECTIONS

[75] Inventor: Aldo Garzia, Lodi (Milan), Italy

[73] Assignee: Istituto Chemioterapico Italiano S.p.A., Italy

[22] Filed: Nov. 6, 1974

[21] Appl. No.: 521,383

Related U.S. Application Data

[60] Division of Ser. No. 364,025, May 25, 1973, Pat. No. 3,882,105, which is a continuation-in-part of Ser. No. 309,483, Nov. 24, 1972, abandoned.

[52] U.S. Cl. .................................................. 424/251
[51] Int. Cl.² ......................................... A61K 31/505
[58] Field of Search ..................................... 424/251

[56] References Cited
UNITED STATES PATENTS 3,686,203  5/1969  Somerset et al. .................... 260/309

FOREIGN PATENTS OR APPLICATIONS 2,015,181  2/1970  France ........................... 260/240 E

*Primary Examiner*—Jerome D. Goldberg
*Attorney, Agent, or Firm*—Morton, Bernard, Brown, Roberts & Sutherland

[57] ABSTRACT

This invention relates to 2-amino-4-[2-(1-lower alkyl-5-nitro-2-imidazolyl)vinyl]-pyrimidines and their use in the treatment of protozoal diseases and bacterial infections.

14 Claims, No Drawings

2-AMINO-4[2-(1-LOWER ALKYL-5-NITRO-2-IMIDIAZOLYL)VINYL]-PYRIMIDINES FOR TREATING PROTOZOAL AND BACTERIAL INFECTIONS

This application is a division of application Ser. No. 364,025, filed May 25, 1973, now U.S. Pat. No. 3,882,105, which in turn is a continuation-in-part of application Ser. No. 309,483, filed Nov. 24, 1972, now abandoned said application incorporated herein by reference.

This invention relates to novel compounds, processes for their preparation, and methods for their use in the therapeutic treatment of hosts afflicted with protozoal diseases and bacterial infections. More particularly, this invention is directed to 2-amino-4-[2-(1-lower alkyl-5-nitro-2-imidazolyl)-vinyl]-pyrimidines as the novel compounds. The methods involve their antiprotozoal (e.g., anti-amebic) activity against pathogenic protozoa, and their anti-bacterial activity against pathogenic bacteria in living warm blooded animal bodies.

The novel compounds, which are active antiprotozoal and antibacterial agents, are particularly effective in therapeutically treating trichomoniasis, for instance, vulvovaginitis caused by Trichomonas vaginalis, by inhibiting the growth of or destroying the microorganism (pathogenic protozoa) causing the disease. The compounds are also provided for the therapeutic treatment of bacterial infections caused by, for instance, microorganisms (pathogenic bacteria) such as Brucella brochiseptica, Salmonella pullorum, Streptococcus pyogenes, Diplococcus pneumoniae, Klesiella pneumoniae, and others, which microorganisms are inhibited in growth or destroyed by these compounds.

In one aspect, this invention relates to a method of treating vulvovaginitis, which is often caused by the protozoa Trichomonas vaginalis, and occurs in the female population with a high frequency and in males. Therefore, efforts have been put forth in searching for antitrichomonal agents which are very efficacious and non-toxic and, when administered to pregnant women, do not influence the regular development of the fetus. Desirably, the antitrichomonal agent should not adversely affect normal vaginal microflora, including Bacillus doderlein (Lactobacillus acidophilus).

Metronidazole, 1-(2-hydroxyethyl)-2-methyl-5-nitroimidazole, has been proposed for use as an antitrichomonal agent by Jacob et al. in U.S. Pat. No. 2,944,061, and is presently a frequently prescribed, commercially available drug for the treatment of vulvovaginitis. Although metronidazole is commonly employed for treatment of trichomoniasis, it has not been found to be completely satisfactory since certain strains of Trichomonas vaginalis have developed a resistance to the drug. Other proposals include the use of certain 1-lower alkyl-2-(2-substituted vinyl)-5-nitroimidazoles as an intermediate to sulfur-containing anitprotozoal agents by Miller et al. in U.S. Pat. No. 3,549,626, and the use of certain 2-(5-nitro-2-furyl)-vinyl pyrimidine derivatives as antitrichomonal agents by Minami et al. in U.S. Pat. No. 3,464,982.

An object of this invention is the provision of 2-amino-4-[2-(1-lower alkyl-5-nitro-2-imidazolyl)-vinyl]-pyrimidines (hereafter the "P-Compounds"), which may be represented by the structural formula

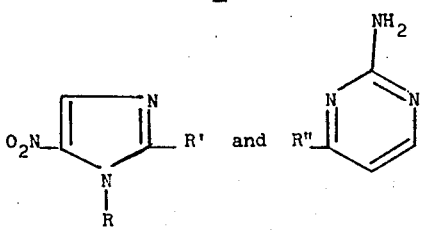

wherein R is lower alkyl of 1 to about 6, preferably 1 to about 3, carbon atoms, to provide antiprotozoal and antibacterial activity, and especially to provide these P-Compounds for the treatment of vulvovaginitis. Exemplary of the P-Compounds are 2-amino-4-[2-(1-methyl-5-nitro-2-imidazolyl)-vinyl]-pyrimidine, 2-amino-4-[2-(1-ethyl-5-nitro-2-imidazolyl)-vinyl]-pyrimidine, 2-amino-4-[2-(1-propyl-5-nitro-2-imidazolyl)-vinyl]-pyrimidine, 2-amino-4-[2-(1-pentyl-5-nitro-2-imidazolyl)-vinyl]-pyrimidine, and the like.

One, or a combination, of the P-Compounds may be therapeutically administered, in microorganism-growth inhibiting amounts, to a living warm blooded animal suffering from a protozoal disease or a bacterial infection caused by a microorganism. They may be administered to the subject in any convenient form, for instance, in a pharmaceutical composition comprising a pharmaceutically-acceptable carrier and one or more of the P-Compounds, and exhibit activity in the urine and in the serum.

The P-Compounds are very efficacious against Trichomonas vaginalis even at low concentrations, say, at a concentration of about 1 or 2 micrograms per milliliter in in vitro tests. The amount of a P-Compound administered to a human patient suffering from trichomoniasis may frequently be from about 50 to about 2000 milligrams per day, especially for an individual weighing about 50 to 70 kilograms.

The protozoal diseases and bacterial infections which may be treated by the method of this invention include, as protozoal diseases, trichomoniasis, enterohepatitis, amoebiasis, trypanosomiasis and enteric protozoal diseases, and, as bacterial infections, important Gram positive and Gram negative strains of pathogenic bacteria, particularly members of the coccus form of bacteria, including species of Diplococcus, Streptococcus and the like; and, for instance, species of Salmonella, Brucella, Klebsiella; and pleuropneumonia-like organisms (PPLO), the growth of which are inhibited by the P-Compounds. These compounds do not damage normal vaginal microflora, including Bacillus doderlein (Lactobacillus acidophilus).

The P-Compounds may be produced by a number of syntheses, for instance, by a dehydration reaction between

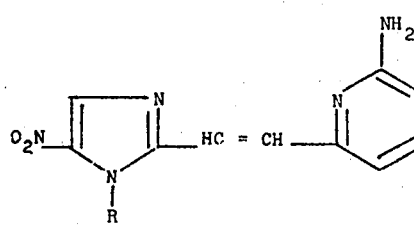

wherein R is lower alkyl, as previously designated, and one of R' and R" is

and the other is —CH₃. The reaction is conducted in the presence of dehydrating amounts of a dehydrating agent under dehydrating conditions including temperatures which promote the dehydration reaction to react the formyl group and methyl group to yield water and provide the desired P-Compound. The dehydration conditions generally include ambient pressures and temperatures ranging from about 25° to 150°C., preferably from about 30° to 90°C.

The dehydrating agent is preferably a strong mineral acid and is advantageously employed in excess of that stoichiometrically required for completion of the reaction. Exemplary of strong mineral acids suitable for use as dehydrating agents are sulfuric acid, hydrochloric acid, phosphoric acid, and the like. Other acids, e.g., aromatic sulfonic acids containing from about 6 to 11 carbon atoms, such as para-toluene sulfonic acid, can be used. Lower fatty acid anhydrides, e.g., acetic anhydride, can also be used. The dehydrating agent can also be used as a solvent as well in solvent-providing amounts. Generally, the amount of dehydrating agent employed is at least about 1.1 times the stoichiometric amount required for completion of the reaction and may be 20 or 30 or more times that required for completion of the reaction when the dehydrating agent serves also as the solvent medium for the reaction. Greater amounts may be employed, but such amounts would appear to be impractical.

Suitable solvents are usually employed, preferably an organic carboxylic acid, e.g., an acyclic saturated monoacid containing from 1 to about 6 carbon atoms such as acetic or propionic acids, and among these, glacial acetic acid is preferred. The solvent is frequently provided in a weight ratio to the reactants including the dehydrating agent of at least about 2:1, preferably about 3:1 to 10:1, although greater amounts may be employed.

A particularly advantageous process for making the P-Compounds comprises reacting 5-nitro-1-lower alkyl-2-formyl imidazole, where the lower alkyl group corresponds to the lower alkyl group at the 1 position on the imidazolyl nucleus. For instance, one process for the preparation of 2-amino-4-[2-(1-methyl-5-nitro-2-imidazolyl)-vinyl]-pyrimidine (the "P'-Compound") comprises reacting 5-nitro-1-methyl-2-formyl imidazole with 2-amino-4-methyl pyrimidine to provide the P'-Compound. The 2-amino-4-methyl pyrimidine may be used in a slight stoichiometric excess, e.g., about 1 to 50 weight percent in excess of that required to react with the imidazole reactant, and the reaction is advantageously conducted in the presence of a dehydrating agent, preferably at temperatures from about 30° to 90°C., advantageously from about 35° to 75°C. The resultant reaction mixture may be diluted with water and neutralized with a suitable base, for instance, a saturated solution of sodium bicarbonate, to form the novel compound as a precipitate.

5-Nitro-1-lower alkyl-2-formyl imidazole is disclosed in Henry et al., U.S. Pat. No. 3,472,864, and several methods of its preparation are disclosed therein. For instance, 5-nitro-1-methyl-2-formyl imidazole can be prepared by contacting 5-nitro-1,2-dimethyl imidazole with selenium dioxide, and heating the mixture until the reaction begins, as indicated by the evolution of heat. On conclusion of the exothermic reaction, the mixture is cooled, and the imidazoles are separated by extraction into an organic solvent. A final purification may be facilitated by the formation of an insoluble aldehyde derivative such as an oxime, hydrazone, or semicarbazone. Another method of obtaining 5-nitro-1-methyl-2-formyl imidazole is by the reaction of 1-methyl-5-nitroimidazole with trioxymethylene in a dimethyl sulfoxide solution in a sealed tube to form 1-methyl-2-hydroxymethyl-5-nitroimidazole which can be oxidized with an oxidant such as lead tetraacetate, manganese dioxide, nitrogen tetroxide, dimethylsulfoxide-dicyclohexyl carbodiimide, nitric acid or pyridine-chromium trioxide complex or with other reagents capable of converting the 2-hydroxymethyl substituent to a 2-formyl radical.

2-Amino-4-methyl pyrimidine can be obtained from the reaction of guanidine hydrochloride and chlorovinylmethyl ketone as is well known in the art, and the compound is reported, for instance, as compound P-2100 in *The Handbook of Chemistry and Physics*, 46th edition, page C-523. Other preparations of pyrimidine may be found in, for instance, Gillman, *Organic Chemistry An Advanced Treatise*, Volume 4, page 866 et seq. (1953).

Another process for preparation of the P-Compounds comprises reacting 2-amino-4-(dialkoxymethyl)-pyrimidine, a precursor to 2-amino-4-formyl-pyrimidine, where the alkoxy groups may be the same or different and may be lower alkoxy of 1 to about 6 carbon atoms, preferably ethoxy, with 1-lower alkyl-2-methyl-5-nitroimadazole wherein the lower alkyl group corresponds to the lower alkyl substituent of the compound. The acetal structure, in the presence of aldehyde-forming amounts of water, will provide the corresponding aldehyde and alcohol. The conversion of the acetal to aldehyde may occur in the same reaction simultaneously with the dehydration reaction to provide the P-Compounds, or the aldehyde may be prepared prior to conducting the reaction with the imidazole component to provide the P-Compounds.

The amount of water available for reaction with the acetal should preferably be in excess of the stoichiometric amount required to provide the desired amount of pyrimidine component for the reaction to produce the P-Compounds. For instance, when the acetal is being reacted in the presence of the imidazole component, thus the 2-amino-4-formyl-pyrimidine is being prepared in situ, the water liberated from the dehydration reaction may serve to react with the acetal on the pyrimidine group. It may be desirable to employ only catalytically-effective amounts of water to initiate the reactions, for instance, about 0.01 or 1 to 50 percent of the amount of water required to provide the desired amount of aldehyde. Excessive amounts of water may reduce the effectiveness of the dehydrating agent. Since the acetal and aldehyde are in an equilibrium relationship, it is often preferable to provide the acetal in an amount in excess of that stoichiometrically required for reaction with the imidazole component in order to favor the production of the aldehyde, for instance, about 1.1 to 5 times the amount required. If the acetal is converted to the aldehyde prior to conducting the reaction between the pyrimidine and imidazole components to prepare the P-Compounds of this invention, the water may be employed in excess of the amount stoichiometrically required for the desired degree of conversion, e.g., about 1.1 to 10, preferably 1.5 to 5, times the amount required. Generally, a temperature in the range of about 25° to 150°C. may be employed. For example, the P'-Compound (where R is methyl) can be prepared through the reaction of 2-amino-4-(diethoxymethyl) pyrimidine, which is described in *J. Am. Chem. Soc.*, Volume 69, page 3072 (1947), with 1,2-dimethyl-5-nitroimidazole, which is described in *J. Chem. Soc.*, Volume 127, page 1832 (1925).

The dehydration reaction to provide the P-Compounds may be conducted in two stages. First, the aldehyde and methyl group may be reacted in the presence of a strong base in excess of the amount stoichiometrically required for reaction, e.g., about 1.1 or 1.5 to 10 to 15 times, to form a secondary alcohol, and then the secondary alcohol can be dehydrated with a dehydrating agent as described above.

The P-Compounds may be administered, for therapeutical purposes, to a host in any convenient manner. For example, one of the P-Compounds may be topically applied on the affected area, orally administered, or parenterally administered, for instance, by cutaneous, subcutaneous, intravenous, and the like, injections. Oral and topical treatments are generally preferred for vulvovaginitis due to the ease of administration. Generally, the amount of a P-Compound administered to a human patient to achieve antitrichomonal activity is about 50 to 2000 milligrams per day, especially for an individual weighing about 50 to 70 kilograms. In females, the amount administered is preferably from about 200 to 1000 milligrams per day, and for males, about 100 to 800 milligrams per day is preferred. Normally, the dosage amount in treating living warm-blooded animal bodies having a protozoal disease or bacterial infection which is therapeutically-responsive to a P-Compound is about 1 to 40, preferably about 4 to 20, milligrams of the compound per kilogram of body weight per day. A P-Compound may be administered once a day, or fractionally at periodic intervals throughout the day. When orally administered, two or three or more fractional doses per day are preferred.

For oral administration, a P-Compound is usually compounded in a pharmaceutical unit dosage form such as pill, lozenge, tablet or capsule with a pharmaceutically-acceptable carrier. Such unit dosage forms, for example, containing from about 50 to about 500 milligrams of a P-Compound, are quite satisfactory and are prepared according to techniques known to those skilled in the art. Thus, these unit dosage forms will contain the normal diluents, excepients, lubricating agents, and extenders regularly employed in compounding such forms. Exemplary carriers are solids such as lactose, magnesium stearate, calcium stearate, starch, terra alba, dicalcium phosphate, sucrose, talc, stearic acid, gelatin, agar, pectin, or acacia.

Alternatively, a P-Compound may be suspended in or dissolved in liquid vehicles suitable for oral administration. The final preparation may be in the form of a solution, emulsion, suspension, syrup, or the like. Liquid carriers which may be employed include, for instance, peanut oil, sesame oil, olive oil, water, and the like. The liquid preparation may also include wetting agents and other conventional additives for liquid pharmaceutical dosage forms.

For topical administration, topical jellies, creams, ointments, or suppositories are normally used. Vaginal inserts containing, as inactive ingredients, lactose, starch, hydrogenated castor oil, polyvinyl alcohol or other water soluble non-toxic polymer, and the like are commonly used. Vaginal inserts are normally used once a day for convenience and are often supplemented with, for instance, oral administration of a P-Compound.

A P-Compound may also be contained in a suitable, sterile solution or suspension in a pharmaceutically-acceptable carrier for parenteral injections. In addition, P-Compounds used in the method of this invention for inhibiting the growth of or destroying microorganisms which cause protozoal diseases or bacterial infections, or in compositions containing the same, may be either administered in amounts sufficient to produce the desired anti-protozoal or anti-bacterial effects upon administration of a unit dosage form of one or more P-Compounds, together with or include other physiologically active materials and/or medicants, e.g., buffering agents, antacids, sedatives, tranquilizers, analgesics, or the like.

The P-Compounds also may be used in veterinary medicine in the treatment of bacterial and protozoal, particularly trichomonad infections. For instance, they may be used to treat *Trichomonas fetus* in cattle. *Trichomonas fetus* causes abortion and sterility in cattle.

It will be understood that the P-Compounds of this invention as used to treat protozoal or bacterial infections can be brouoght into a unit dosage form by any suitable technique known to one of ordinary skill in the art.

The following examples are provided to further illustrate this invention. All parts and percentages are by weight unless otherwise stated.

EXAMPLE I

Into a mixture of 1.6 grams of 2-amino-4-methylpyrimidine with 10 milliliters of glacial acetic acid is slowly added 2.13 grams of concentrated sulfuric acid. A mixture of 2.4 grams of 2-formyl-1-methyl-5-nitroimidazole in 20 milliliters of glacial acetic acid is slowly added to the mixture of the pyrimidine under stirring. The reaction mixture is maintained at a temperature of about 55°C. for 4 hours. The resultant mixture is then diluted with 200 milliliters of distilled water and neutralized with a saturated aqueous solution of sodium bicarbonate. A brownish-yellow precipitate is formed and recovered. The product is analyzed by infrared spectroscopy and is found to conform to 2-amino-4-[2-(1-methyl-5-nitro-2-imidazolyl)-vinyl]-pyrimidine.

EXAMPLE II

In vitro tests to determine the activity of 2-amino-4-[2-(1-methyl-5-nitro-2-imidazolyl)-vinyl]-pyrimidine against *Trichomonas vaginalis* are conducted using three strains of the protozoa: Serafino Belfonti strain, hereinafter designated as S, obtained from the Institute of Serum Therapy of Milan, and strains C1 and C2, obtained from Professor Cantoni of the Institute of Inspection of Foods of Animal Origin of the University of Milan. The medium for the maintenance of the strains is of the type disclosed as the Simplified Tripticase Serum by Kupferberg et al. in *Proceedings of the Society of Experimental Biological Medicine*, Volume 67, p. 304, 1948, to which 0.1 weight percent of chloramphenicol has been added. The chloramphenicol serves to impede the development of contaminating bacteria, but is inactive against *Trichomonas vaginalis* at this low concentration. Prior to use, the medium is raised to a temperature of 100°C. for about 2 to 3 minutes to remove a significant amount of oxygen from the medium. After cooling to about 37° C., 0.5 weight percent of human serum is added under sterile conditions. To about 9 milliliters of this medium is added about 0.25 to 0.30 milliliter of the previous broth, and transfers to new broths for the maintenance of the strains are carried out every 48 to 72 hours. The incubation of the strains is at 37°C.

The three strains are employed to determine the efficacy of 2-amino-4-[2-(1-methyl-5-nitro-2-imidazolyl)-vinyl]-pyrimidine by transferring a standard 0.25 to 0.30 milliliter inoculum to a new 9 milliliter broth containing 0.5, 1.0, 1.5 or 2.0 micrograms of the compound per milliliter. After 48 to 72 hours, the broth is examined visually for the degree of turbidity in the culture tubes, and thus the development of the protozoa. The turbidity due to the coagulation of the protein of the serum is distinguished from the development of the protozoa due to the decolorization of the medium since the development of the protozoa is accompanied by a reduction of the methylene blue in the medium. The broth is also examined using a phase contrast microscope to evaluate the degree of mobility or lack of mobility of the *Trichomonas vaginalis*. The microscopic examinations also show the morphology of the cells in that young cells have a pear-shaped structure whereas older cells are more rounded. As a comparison, identical tests are conducted using metronidazole as the active ingredient. Controls are run using no active ingredient. The results are provided in Tables 1 to 6 wherein the following symbols are employed: 2-amino-4-[2-(1-methyl-5-nitro-2-imidazolyl)-vinyl]-pyrimidine (P'-Compound) is represented as F; metronidazole, MET; cells very mobile, VM; cells mobile, M; cells slightly mobile, SM; cells immobile or absent, I; culture very turbid, VT; culture turbid, T; culture slightly turbid, ST; culture clear, C.

TABLE 1

*Trichomonas vaginalis* - Strain S -
Microscopic Examination

| | Run | Control | 0.5 | 1.0 | 1.5 | 2.0 |
|---|---|---|---|---|---|---|
| F | I | VM | VM | SM | I | I |
|   | II | VM | VM | SM | I | I |
|   | III | VM | VM | SM | I | I |
| MET | I | VM | VM | M | SM | I |
|   | II | VM | VM | M | SM | I |
|   | III | VM | VM | M | SM | I |
| | | Culture Appearance | | | | |
| F | I | VT | T | ST | C | C |
|   | II | VT | T | ST | C | C |
|   | III | VT | T | ST | C | C |
| MET | I | VT | VT | T | ST | C |
|   | II | VT | VT | T | ST | C |
|   | III | VT | VT | T | ST | C |

TABLE 2

*Trichomonas vaginalis* - Strain S -
Microscopic Examination

| | Run | Control | 0.5 | 1.0 | 1.5 | 2.0 |
|---|---|---|---|---|---|---|
| F | I | VM | SM | I | I | I |
|   | II | VM | SM | I | I | I |

TABLE 2-continued

*Trichomonas vaginalis* - Strain S -
Microscopic Examination

| | Run | Control | 0.5 | 1.0 | 1.5 | 2.0 |
|---|---|---|---|---|---|---|
|   | III | VM | SM | I | I | I |
| MET | I | VM | M | M | SM | I |
|   | II | VM | M | M | SM | I |
|   | III | VM | M | M | SM | I |
| | | Culture Appearance | | | | |
| F | I | VT | ST | ST | C | C |
|   | II | VT | ST | C | C | C |
|   | III | VT | ST | C | C | C |
| MET | I | VT | T | T | T | ST |
|   | II | VT | T | T | T | ST |
|   | III | VT | T | T | T | ST |

TABLE 3

*Trichomonas vaginalis* - Strain S -
Microscopic Examination

| | Run | Control | 0.5 | 1.0 | 1.5 | 2.0 |
|---|---|---|---|---|---|---|
| F | I | VM | SM | I | I | I |
|   | II | VM | SM | I | I | I |
|   | III | VM | SM | I | I | I |
| MET | I | VM | M | M | M | I |
|   | II | VM | M | M | M | I |
|   | III | VM | M | M | M | M |
| | | Culture Appearance | | | | |
| F | I | VT | ST | C | C | C |
|   | II | VT | T | C | C | C |
|   | III | VT | T | C | C | C |
| MET | I | VT | T | T | ST | C |
|   | II | VT | T | T | ST | C |
|   | III | VT | T | T | ST | ST |

TABLE 4

*Trichomonas vaginalis* - Strain S -
Microscopic Examination

| | Run | Control | 0.5 | 1.0 | 1.5 | 2.0 |
|---|---|---|---|---|---|---|
| F | I | VM | I | I | I | I |
|   | II | VM | I | I | I | I |
|   | III | VM | I | I | I | I |
| MET | I | VM | VM | I | I | I |
|   | II | VM | M | SM | I | I |
|   | III | VM | M | SM | I | I |
| | | Culture Appearance | | | | |
| F | I | VT | C | C | C | C |
|   | II | VT | C | C | C | C |
|   | III | VT | ST | C | C | C |
| MET | I | VT | T | C | C | C |
|   | II | VT | T | ST | C | C |
|   | III | VT | T | ST | C | C |

TABLE 5

*Trichomonas vaginalis* - Strain C1 -
Microscopic Examination

| | Run | Control | 0.5 | 1.0 | 1.5 | 2.0 |
|---|---|---|---|---|---|---|
| F | I | VM | SM | I | I | I |
|   | II | VM | I | I | I | I |
|   | III | VM | SM | I | I | I |
| MET | I | VM | M | M | SM | I |
|   | II | VM | M | M | SM | I |
|   | III | VM | M | M | SM | I |

TABLE 5-continued

Trichomonas vaginalis - Strain C1 -
Microscopic Examination

|   | Run | Control | 0.5 | 1.0 | 1.5 | 2.0 |
|---|---|---|---|---|---|---|
|   |   | Culture Appearance | | | | |
| F | I | VT | ST | C | C | C |
|   | II | VT | ST | C | C | C |
|   | III | VT | ST | C | C | C |
| MET | I | VT | T | T | ST | C |
|   | II | VT | T | T | ST | C |
|   | III | VT | T | T | ST | C |

TABLE 6

Trichomonas vaginalis - Strain C2 -
Microscopic Examination

|   | Run | Control | 0.5 | 1.0 | 1.5 | 2.0 |
|---|---|---|---|---|---|---|
| F | I | VM | SM | I | I | I |
|   | II | VM | I | I | I | I |
|   | III | VM | SM | I | I | I |
| MET | I | VM | VM | M | SM | I |
|   | II | VM | VM | M | SM | I |
|   | III | VM | M | M | SM | I |
|   |   | Culture Appearance | | | | |
| F | I | VT | ST | C | C | C |
|   | II | VT | C | C | C | C |
|   | III | VT | T | C | C | C |
| MET | I | VT | VT | T | T | C |
|   | II | VT | VT | T | T | C |
|   | III | VT | VT | T | T | C |

The results summarized in Example II illustrate that the P'-Compound inhibits *Trichomonas vaginalis*, including resistant strains of the microorganism, at a substantially lower concentration in the in vitro test, than metronidazole.

EXAMPLE III

2-Amino-4[2-(1-methyl-5-nitro-2-imidazolyl)-vinyl]pyrimidine is tested to determine its effect in vitro on mature cultures of *Trichomonas vaginalis*. Nine milliliter samples of strains S, C1, and C2 of *Trichomonas vaginalis are prepared in accordance with Example II and incubated for* 48 hours. The cultures are then transferred to sterile tubes containing the same concentrate of active compound as in Example II. Microscopic evaluations for mobility are conducted after 24 and 48 hours of incubation after the addition of the active compound. The results are provided in Tables 7 and 8 with the same symbols being employed as in Tables 1 to 6. Visual evaluation of the broth is not taken into consideration due to the nature of the test.

TABLE 7

Microscopic evaluation at 24 hours after
addition of active compound

|   | Strains | Control | 0.5 | 1.0 | 1.5 | 2.0 |
|---|---|---|---|---|---|---|
| F | S | VM | M | SM | SM | SM |
|   | C1 | VM | SM | SM | SM | SM |
|   | C2 | VM | M | SM | SM | SM |
| MET | S | VM | VM | M | M | SM |
|   | C1 | VM | M | M | M | SM |
|   | C2 | VM | M | M | M | SM |

TABLE 8

Microscopic evaluation at 48 hours after
addition of active compound

|   | Strains | Control | 0.5 | 1.0 | 1.5 | 2.0 |
|---|---|---|---|---|---|---|
| F | S | M | SM | SM | SM | I |
|   | C1 | M | SM | SM | I | I |
|   | C2 | M | SM | SM | SM | I |
| MET | S | M | M | M | M | I |
|   | C1 | M | M | M | SM | I |
|   | C2 | M | M | M | M | I |

The results summarized in Example III illustrate that the P-Compounds inhibit *Trichomonas vaginalis*, including resistant strains of the microorganism, at substantially lower concentrations in vitro tests than metronidazole.

EXAMPLE IV

The activity of 2-amino-4-[2-(1-methyl-5-nitro-2-imidazolyl)-vinyl]-pyrimidine against certain other microorganisms is determined by the use of the well known streak plate method. The microorganisms are obtained from a 24-hour slant of Difco Brain Heart Infusion Agar which is incubated at 37°C. The streaks are made with a suspension of the microorganism in 5 to 6 milliliters of sterile physiological solution. In the case of the strains belonging to the group of mycetes, Difco Malt Agar broth is used and incubation is at 30°C. The streaks so prepared, are incubated for 24 hours. The results are provided in Table 9.

TABLE 9

| Microorganism | Minimal inhibitory concentration (microgram of active compound per milliliter of broth) | |
|---|---|---|
|   | F | MET |
| Aerobacter aerogenes 20 (1) | >100 | >100 |
| Bacillus cereus var. mycoides ATCC 9634 | <12.5–25 | >100 |
| Bacillus subtilis ATCC 6633 | <12.5 | >100 |
| Brucella bronchiseptica | <12.5 | >100 |
| Escherichia coli 46 (1) | >100 | >100 |
| Micrococcus flavus ATCC 10240 | >100 | >100 |
| Proteus mirabilis 61 (1) | >100 | >100 |
| Proteus vulgaris ATCC 6897 | >100 | >100 |
| Pseudomonas aeruginosa 77 (1) | >100 | >100 |
| Salmonella pullorum ATCC 9120 | <12.5 | >100 |
| Salmonella typhimurium | >100 | >100 |
| Shigella dissenteriae Madsen (1) | >100 | >100 |
| Staphylococcus aureus 168 (1) (2) | >100 | >100 |
| Streptococcus faecalis | >100 | >100 |
| Streptococcus pyogenes | <12.5 | >100 |
| Diplococcus pneumoniae | <12.5 | >100 |
| Klebsiella pneumoniae | <12.5 | >100 |
| Candida albicans | >100 | >100 |
| Schizosaccharomyces pombe | >100 | >100 |
| Aspergillus niger | >100 | >100 |
| Aspergillus flavus | >100 | >100 |

(1) Virulent strain isolated in hospital
(2) Penicillin-resistant strain

It is demonstrated through Example IV that the P-Compounds can be classified a limited spectrum anti-bacterial agent in that microorganisms which are Gram positive as well as a few Gram negative types are inhibited at 12.5 µg/ml or less.

EXAMPLE V

Four female patients suffering from vulvovaginitis are orally administered 2-amino-4-[2-(1-methyl-5- nitro-2-imidazolyl)-vinyl]-pyrimidine in the amount of 500 milligrams per day. Two of the patients continue the treatment for 1 day, and the other two continue the treatment for 3 days. Urine samples are taken and are evaluated to determine the concentration of the active compound therein. In all cases, the concentration of the active compound in the urine is maintained at least three times as much as the average concentration required to kill Trichomonas vaginalis in vitro.

EXAMPLE VI

Six female patients who are to undergo colpohysterectomy are orally administered two capsules containing 250 milligrams of 2-amino-4-[2-(1-methyl-5-nitro-2-imidazolyl)-vinyl]-pyrimidine each per day for a few days prior to surgery. The concentration of the active compound is determined microbiologically using plates of vaginal homogenates. The concentration is found to be about 8 micrograms per gram of homogenate.

EXAMPLE VII

Thirty female patients suffering from vulvovaginitis and having Trichomonas vaginalis present in the vaginal secretion, are orally administered two capsules containing 250 milligrams of 2-amino-4-[2-(1-methyl-5-nitro-2-imidazolyl)-vinyl]-pyrimidine each per day. After 5 days, the presence of Trichomonas vaginalis is not found, and no sign of leukorrhea is observed, evidencing successful treatment. In comparison, using metronidazole administered orally in the same amount, 10 days of medication are usually required for complete treatment.

As with other imidazole-containing drugs, some secondary effects may be reported in select cases such as nausea, diarrhea, bad breath, urticaria, uretheral and vaginal burning, dizziness, headache, insomnia, and in rare cases, temporary leucopenia.

EXAMPLE VIII

Example I is repeated except employing as reactants 1,2-dimethyl-5-nitroimidazole and 2-amino-4-(diethoxymethyl)-pyrimidine. The concentrated sulfuric acid (98%) provides sufficient water to initiate and sustain the conversion of the diethoxymethyl group on the pyrimidine to a formyl group and ethanol, and 2-amino-4-[2-(1-methyl-5-nitro-2-imidazolyl)-vinyl]-pyrimidine is formed in situ.

EXAMPLE IX

Example I is repeated except employing, as reactants, 2-amino-4-methyl pyrimidine and 2-formyl-1-ethyl-5-nitroimidazole. 2-Amino-4-[2-(1-ethyl-5-nitro-2-imidazolyl)-vinyl]-pyrimidine is formed. It is recovered and a sample is used to in vitro inhibit the growth of Trichomonas vaginalis in accordance with Example II. Another sample is used to form a dosage unit capsule of 250 milligrams, and two capsules per day are orally administered to therapeutically treat a patient suffering from trichomoniasis.

EXAMPLE X

Example I is repeated except employing, as reactants, 2-amino-4-methyl pyrimidine and 2-formyl-1-pentyl-5-nitroimidazole. 2-Amino-4-[2-(1-pentyl-5-nitro-2-imidazolyl)-vinyl]-pyrimidine is formed. It is recovered and a sample is used to in vitro inhibit the growth of Trichomonas vaginalis in vitro tests in accordance with Example II. Another sample is used to form a dosage unit capsule of 250 milligrams, and two capsules per day are orally administered to therapeutically treat a patient suffering from trichomoniasis.

It is claimed:

1. A pharmaceutical composition for therapeutically treating a protozoal disease or bacterial infection in a living, warm-blooded animal body comprising an amount effective to combat the disease or infection of an active ingredient consisting essentially of a compound of the formula

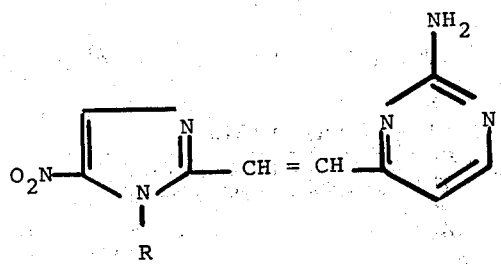

wherein R is lower alkyl of 1 to about 6 carbon atoms and a pharmaceutically acceptable carrier.

2. The pharmaceutical composition of claim 1, wherein the active ingredient is 2-amino-4-[2-(1-methyl-5-nitro-2-imidazolyl)-vinyl]-pyrimidine.

3. The pharmaceutical composition of claim 1 in suitable form for oral administration.

4. A method for therapeutically treating a protozoal disease or bacterial infection from members of the coccus form of bacteria, species of Brucella, Salmonella, Klebsiella, or pleuropneumonia-like organisms in a living, warm-blooded body comprising therapeutically administering, to the body, a compound of the formula

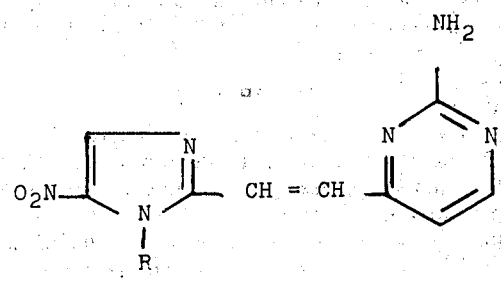

wherein R is lower alkyl of 1 to about 6 carbon atoms, in an amount effective to combat the disease or infection.

5. The method of claim 4 wherein the animal body has as the protozoal disease, trichomoniasis, enterohepatitis, trypanosomiasis, amoebiasis, or enteric protozoal disease.

6. The method of claim 4 wherein the amount of said compound administered to the body is about 1 to 40 milligrams per kilogram of body weight per day.

7. The method of claim 4, wherein 2-amino-4-[2-(1-methyl-5-nitro-2-imidazolyl)-vinyl]-pyrimidine is administered.

8. The method of claim 7 wherein the animal body has trichomoniasis and the compound is administered in an amount of about 1 to 40 milligrams per kilogram of body weight per day.

9. The method of claim 4 wherein the compound is administered orally.

10. A method of treating a human patient having trichomoniasis comprising therapeutically administering to the patient, a compound of the formula

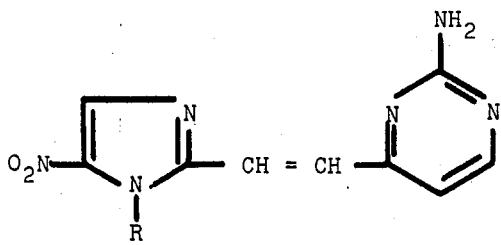

wherein R is lower alkyl of 1 to about 6 carbon atoms in an amount of about 50 to 2000 milligrams per day.

11. The method of claim 10 wherein 2-amino-4-[2-(1-methyl-5-nitro-2-imidazolyl)-vinyl]-pyrimidine is the compound administered.

12. The method of claim 11 wherein the compound is administered orally.

13. The method of claim 11 wherein the human patient is a female human patient and the compound is therapeutically administered in an amount of about 200 to 1000 milligrams per day.

14. The method of claim 11 wherein the human patient is a male human patient and the compound is therapeutically administered in an amount of about 100 to 800 milligrams per day.

* * * * *

UNITED STATES PATENT AND TRADEMARK OFFICE
CERTIFICATE OF CORRECTION

PATENT NO. : 3,969,520
DATED : July 13, 1976
INVENTOR(S) : ALDO GARZIA

It is certified that error appears in the above–identified patent and that said Letters Patent are hereby corrected as shown below:

The formula at column 2, lines 1 to 9, should appear at column 2, lines 56 to 65.

The formulae at column 2, lines 56 to 65 should appear at column 2, lines 1 to 9.

Signed and Sealed this

Twenty-eighth Day of September 1976

[SEAL]

Attest:

RUTH C. MASON
*Attesting Officer*

C. MARSHALL DANN
*Commissioner of Patents and Trademarks*